US008258101B2

(12) United States Patent
Cuthbertson

(10) Patent No.: US 8,258,101 B2
(45) Date of Patent: *Sep. 4, 2012

(54) PEPTIDE-BASED COMPOUNDS

(75) Inventor: Alan Cuthbertson, Oslo (NO)

(73) Assignee: GE Healthcare AS, Oslo (NO)

( * ) Notice: Subject to any disclaimer, the term of this patent is extended or adjusted under 35 U.S.C. 154(b) by 55 days.

This patent is subject to a terminal disclaimer.

(21) Appl. No.: 12/814,621

(22) Filed: Jun. 14, 2010

(65) Prior Publication Data

US 2010/0256330 A1    Oct. 7, 2010

Related U.S. Application Data

(60) Division of application No. 10/395,500, filed on Mar. 24, 2003, now Pat. No. 7,737,252, which is a continuation of application No. PCT/NO01/00390, filed on Sep. 25, 2001.

(60) Provisional application No. 60/259,919, filed on Jan. 5, 2001.

(30) Foreign Application Priority Data

Sep. 26, 2000 (NO) .................................. 20004795

(51) Int. Cl.
*A61K 38/12* (2006.01)
*C07K 5/12* (2006.01)

(52) U.S. Cl. ..................... 514/21.1; 514/21.5; 514/21.6; 530/317; 530/327; 530/328; 564/253; 424/1.65; 424/1.69

(58) Field of Classification Search .................. None
See application file for complete search history.

(56) References Cited

U.S. PATENT DOCUMENTS

| | | | |
|---|---|---|---|
| 4,647,447 A | 3/1987 | Gries et al. | |
| 4,770,183 A | 9/1988 | Groman et al. | |
| 4,863,715 A | 9/1989 | Jacobsen et al. | |
| 5,078,985 A | 1/1992 | Rhodes | |
| 5,228,446 A | 7/1993 | Unger et al. | |
| 5,364,613 A | 11/1994 | Sieving et al. | |
| 5,367,080 A | 11/1994 | Toner et al. | |
| 5,387,080 A | 2/1995 | Bouhennicha et al. | |
| 5,846,782 A | 12/1998 | Wickham et al. | |
| 6,559,279 B1 | 5/2003 | Manoharan et al. | 530/322 |
| 7,737,252 B2 * | 6/2010 | Cuthbertson | 530/317 |

FOREIGN PATENT DOCUMENTS

| | | |
|---|---|---|
| EP | 0554213 | 8/1993 |
| EP | 0578083 | 1/1994 |
| WO | WO85/02772 | 7/1985 |
| WO | WO89/00557 | 1/1989 |
| WO | WO90/14103 | 11/1990 |
| WO | WO90/15818 | 12/1990 |
| WO | WO91/15243 | 10/1991 |
| WO | WO92/17212 | 10/1992 |
| WO | WO93/05818 | 4/1993 |
| WO | WO95/14714 | 6/1995 |
| WO | WO95/25543 | 9/1995 |
| WO | WO95/26205 | 10/1995 |
| WO | WO96/09840 | 4/1996 |
| WO | WO96/11023 | 4/1996 |
| WO | WO96/17628 | 6/1996 |
| WO | WO96/23524 | 8/1996 |
| WO | WO97/06791 | 2/1997 |
| WO | WO97/10507 | 3/1997 |
| WO | WO97/25073 | 7/1997 |
| WO | WO97/28830 | 8/1997 |
| WO | WO97/29783 | 8/1997 |
| WO | WO98/10795 | 3/1998 |
| WO | WO98/23297 | 6/1998 |
| WO | WO98/47541 | 10/1998 |
| WO | WO98/54346 | 12/1998 |
| WO | WO98/54347 | 12/1998 |
| WO | WO99/39734 | 8/1999 |
| WO | WO99/40214 | 8/1999 |

OTHER PUBLICATIONS

Munt et al. Solution Structures and Integrin Binding Activities of an RGD Peptide with Two Isomers. Biochemistry 2001, 40, 2373-2378.*
Merrifield, Solid Phase Peptide Synthesis (J. Am. Chem. Soci, 85: 2149 (1964(.
Haubner, et.al, J. Nucl. Med. (1999) 40: 1061-1071.
Ruoslahti, J. Cliln. Invest. 87: 1-5 (1991).

* cited by examiner

*Primary Examiner* — Anish Gupta

(57) ABSTRACT

This invention relates to new peptide-based compounds and their use in therapeutically effective treatments as well as for diagnostic imaging techniques. More specifically the invention relates to the use of such peptide-based compounds used as targeting vectors that bind to receptors associated with angiogenesis, in particular the $\alpha v\beta 3$ integrin receptor. Such contrast agents may thus be used for diagnosis of for example malignant diseases, heart diseases, inflammation-related diseases, rheumatoid arthritis and Kaposi's sarcoma. Moreover such compounds may also be used in therapeutic treatment of these diseases.

4 Claims, No Drawings

PEPTIDE-BASED COMPOUNDS

This application is a divisional filing of U.S. application Ser. No. 10/395,500 filed Mar. 24, 2003, now U.S. Pat. No. 7,737,252, which is a continuation of international application number PCT/NO2001/00390, filed Sep. 25, 2001, which claims priority to U.S. application Ser. No. 60/259,919 filed Jan. 5, 2001 filed and Norwegian application number 20004795 filed Sep. 26, 2000, the entire disclosure of which is hereby incorporated by reference.

This application This invention relates to new peptide-based compounds and their use in therapeutically effective treatments as well as for diagnostic imaging techniques. More specifically the invention relates to the use of such peptide-based compounds used as targeting vectors that bind to receptors associated with angiogenesis, in particular the αvβ3 integrin receptor. Such contrast agents may thus be used for diagnosis of for example malignant diseases, heart diseases, inflammation-related diseases, rheumatoid arthritis and Kaposi's sarcoma. Moreover such compounds may also be used in therapeutic treatment of these diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes which break down the proteins of the basement membrane, as well as inhibitors which limit the action of these potentially harmful enzymes. The other prominent effect of angiogenic factors is to cause endothelial cells to migrate and divide. Endothelial cells which are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodeling of tissues, including wound healing and inflammatory processes. Tumors must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumors, the resulting network of blood vessels is usually disorganised, with the formation of sharp kinks and also arteriovenous shunts. Inhibition of angiogenesis is also considered to be a promising strategy for antitumor therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Further examples of undesired conditions that are associated with neovascularization or angiogenesis, the development or proliferation of new blood vessels are listed in Table 1 below. Reference is also made in this regard to WO98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous alformations, astrocytomas, choriocarcinomas, glioblastomas, gliomas, hemangiomas (childhood, capillary), hepatomas, hyperplastic endometrium, ischemic myocardium, Kaposi sarcoma, macular degeneration, melanoma, neuroblastomas, occluding peripheral artery disease, osteoarthritis, psoriasis, retinopathy (diabetic, proliferative), scleroderma, seminomas, solid tumor formation and ulcerative colitis.

Angiogenesis involves receptors which are unique to endothelial cells. The integrin αvβ3 is one of the receptors that is known to be associated with angiogenesis. Stimulated endothelial cells appear to rely on this receptor for survival during a critical period of the angiogeneic process, as antagonists of the ∀v∃3 integrin receptor/ligand interaction induce apoptosis and inhibit blood vessel growth.

The integrin αvβ3 is a member of a family of transmembrane proteins that act as receptors through which cells can adhere to the extracellular matrix. Integrins are heterodimeric molecules in which the α- and β-subunits penetrate the cell-membrane lipid bilayer. The α-subunit has four $Ca^{2+}$ binding domains on its extracellular chain, and the β-subunit has a number of extracellular cysteine-rich domains.

Many ligands (eg. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. (Ruoslahti, *J. Clin. Invest.*, 87: 1-5 (1991)). Perhaps the most widely studied effect of RGD peptides and mimetics thereof relate to their use as anti-thrombotic agents where they target the platelet integrin GpIIbIIIa.

Inhibition of angiogenesis in tissues by administration of either an αvβ3 or αvβ5 antagonist has been described in for example WO 97/06791 and WO95/25543 using either antibodies or RGD containing peptides. EP 578083 describes a series of mono-cyclic RGD containing peptides and WO 90/14103 describes RGD-antibodies. Haubner et al. in the *J. Nucl. Med.* (1999); 40: 1061-1071 describe a new class of tracer for tumour targeting based on monocyclic RGD containing peptides. Biodistribution studies using whole-body autoradiographic imaging revealed however that the $^{125}$I-labelled peptides had very fast blood clearance rates and predominantly hepatobiliary excretion routes resulting in high background noise.

Cyclic RGD peptides where the RGD moiety is constrained by bridging across the ends of the tripeptide sequence have also been described in WO98/54347 and WO95/14714. Peptides derived from in vivo biopanning (WO97/10507) have been used for a variety of targeting applications. The sequence CDCRGDCFC (RGD-4C), with unidentified bridge positions, has been used to target drugs such as doxirubicin (WO98/10795), nucleic acids and adenoviruses to cells (see WO99/40214, WO99/39734, WO98/54347, WO98/54346, U.S. Pat. No. 5,846,782).

The efficient targeting and imaging of integrin receptors associated with angiogenesis in vivo demands a selective, high affinity RGD based vector which is chemically robust and stable. Furthermore, the route of excretion is an important factor when designing imaging agents in order to reduce problems with background. These stringent conditions are met by the structures containing discrete bridges described in the present invention.

Viewed from one aspect the invention provides new peptide-based compounds as defined by formula I. These compounds have utility as vectors with affinity for the integrin αvβ3 and comprising a linear RGD sequence flanked by two discrete bridges where one or both of the bridges is a disulphide bridge. Such vectors have now shown unexpected activity by improved binding/efficacy compared to known linear RGD peptides. These new peptide-based compounds may be used in therapeutically effective treatments as well as for imaging purposes.

Formula I thus defines peptide-based compounds used as vectors (V) having affinity for the integrin αvβ3. However, depending on the definitions of $R_1$ and $X_{1-8}$, formula I also includes compounds of the formula "V-L-R" where
V is the vector, L is a linker moiety or a bond, and R is a detectable moiety (reporter), e.g. detectable in an imaging procedure, such as in vivo imaging of the human or vascularized non-human animal body (e.g. mammalian, avian or reptilian body), wherein said compound is characterised by the general formula (I)

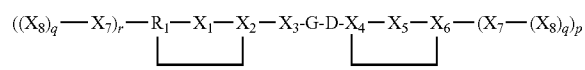

(I)

wherein
r=0 or 1
p=0 or 1
and r+p=1
when r=0 then $R_1$ is —$(CH_2)_n$—CO— or —$(CH_2)_n$—$C_6H_4$—CO— where n=1,2,3,4 or 5,
when r=1 then $R_1$ is or one or more bridge-forming amino acids, preferable cysteine and preferably the bridge between $R_1$ and $X_2$ contains a thioether or a disulphide bond,
and when r=1 (and thus p=0) then $R_1$ is particularly preferably cysteine and forms a disulphide bridge with $X_2$,
$X_1$=a bond or 1, 2, 3, 4 or 5 amino acids, or an amino acid derivatized with a carbohydrate moiety, or an amino acid functionalised with a spacer or linker and/or a chelate binding or capable of binding a reporter suitable for in vivo imaging, preferably a metal radionuclide, preferably $X_1$ is aspartic acid, tyrosine, tyrosine-aspartic acid or lysine,
$X_2$ and $X_4$ are independently cysteine, homocysteine or other amino acids capable of forming a cyclising bond such as aspartic acid and lysine,
$X_3$ is arginine, N-methylarginine or an arginine mimetic,
$X_5$ is a hydrophobic amino acid, preferably phenylalanine, tyrosine, iodotyrosine (most preferably 3-iodo-tyrosine), diiodotyrosine or naphthylalanine,
$X_6$ is an amino acid capable of forming a cyclising bond, preferable cysteine or homocysteine,
$X_7$ is a bond or 1, 2, 3, 4, 5, 6, 7, 8, 9 or 10 amino acids, preferably glycine, or a spacer or linker, optionally allowing for labelling with multiple chelates as defined by $X_8$, and optionally comprising one or more ethylene glycol units or any other spacer component, and $X_8$ is a chelate binding to, or capable of binding a metal radionuclide or any other reporter suitable for in vivo imaging, or is —$NH_2$ or is absent,
q is 0, 1, 2, 3, 4, 5, 6, 7 or 8, and
one of the bridges (between $R_1$ and $X_2$ or between $X_4$ and $X_6$) comprises a disulphide bond.

The vector components of the vector-chelate conjugates described herein have in some aspects of the invention no free amino- or carboxy-termini. Such termini introduce into these compounds a significant increase in resistance against enzymatic degradation and as a result they have an increased in vivo stability as compared to many known free peptides.

The invention relates preferably to a compound of formula (I), further defined by formula (II)

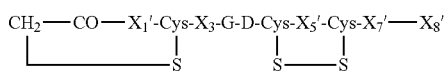

(II)

(II) where Cys=Cysteine
wherein
$X_1'$ is 1, 2 or 3 amino-acids, most preferably aspartic acid, tyrosine, tyrosine-aspartic acid, lysine or acetyl-lysine,
$X_3$ is as defined in formula I;
$X_5'$ is phenylalanine, tyrosine, 3-iodo-tyrosine or naphthylalanine;
$X_7'$ is a bond, glycine, or a O-bis(aminoethyl)ethylene glycol spacer, preferably $X_7$ is glycine; and
$X_8'$ is a chelate binding to a metal radionuclide wherein the structure of the chelate is

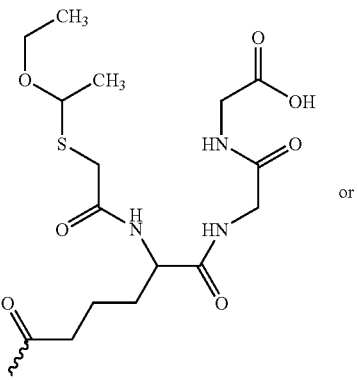 or 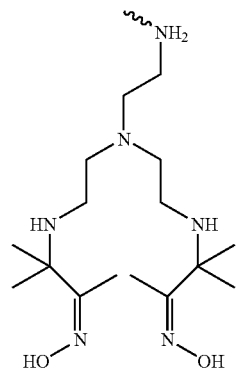

or any other $N_3S$ or bis-oxime type of these chelates, and one bridge comprises a thio bond and the other bridge comprises a disulphide bond as shown in formula II.

In particularly preferred embodiments of the compounds of general formula (II), $X_3$ is N-methyl-arginine and/or $X_5'$ is naphthylalanine.

The reporter, R, may be attached to V (via L) at any suitable point within $X_1$ and/or $X_7$. Preferably, the point of attachment is chosen such that the biological activity of V or the binding affinity of V for its target is not substantially or not significantly reduced (in comparison with the biological activity of V or the binding affinity of V without R). Most preferably, R is attached to V via $X_1$ and/or $X_7$.

As used herein the term 'amino acid' refers in its broadest sense to proteogenic L-amino acids, D-amino acids, chemically modified amino acids, N-methyl, C-methyl and amino acid side-chain mimetics and unnatural amino acids such as naphthylalanine.

The term 'cyclising bond' refers to any combination of amino acids (or with amino acid and $-(CH_2)_n-CO-$ or $-(CH_2)_n-C_6H_4-CO-$) with functional groups which allows for the introduction of a bridge. Some preferred examples are disulphides, disulphide mimetics such as the $-(CH_2)_4-$ carba bridge, thioacetal, thioether bridges (cystathione or lanthionine) and bridges containing esters and ethers.

Some preferred embodiments of the compounds of formula (I) are illustrated by Compounds 1-5 below:

Compound 1:

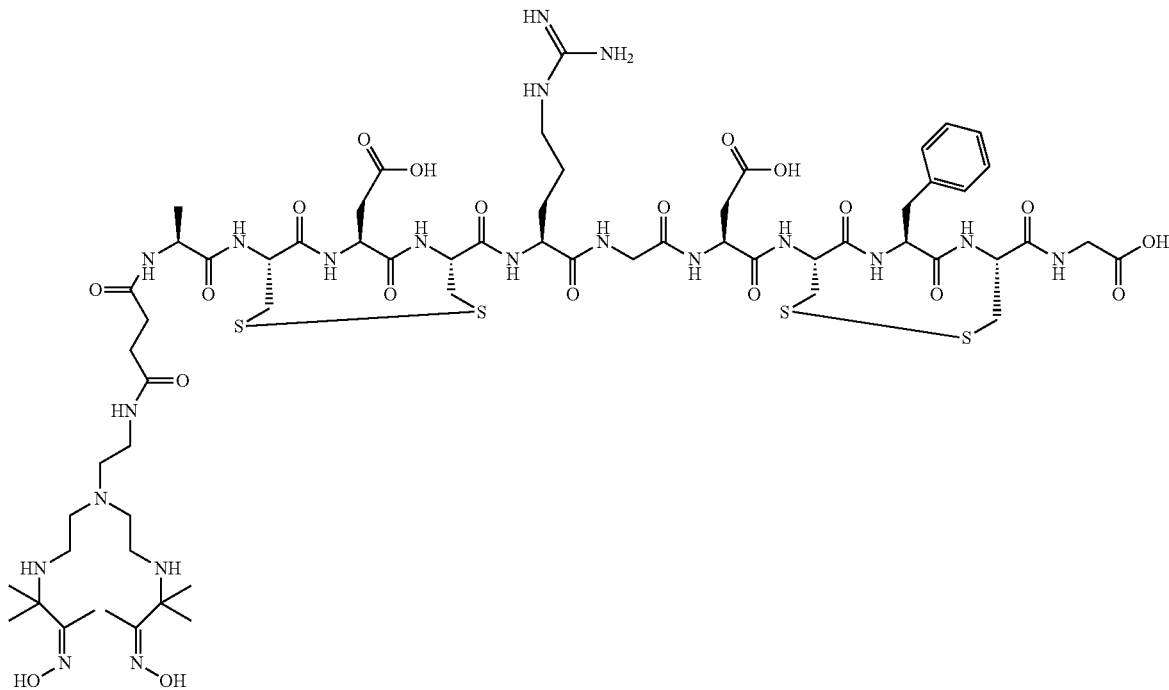

Compound 2: Vector

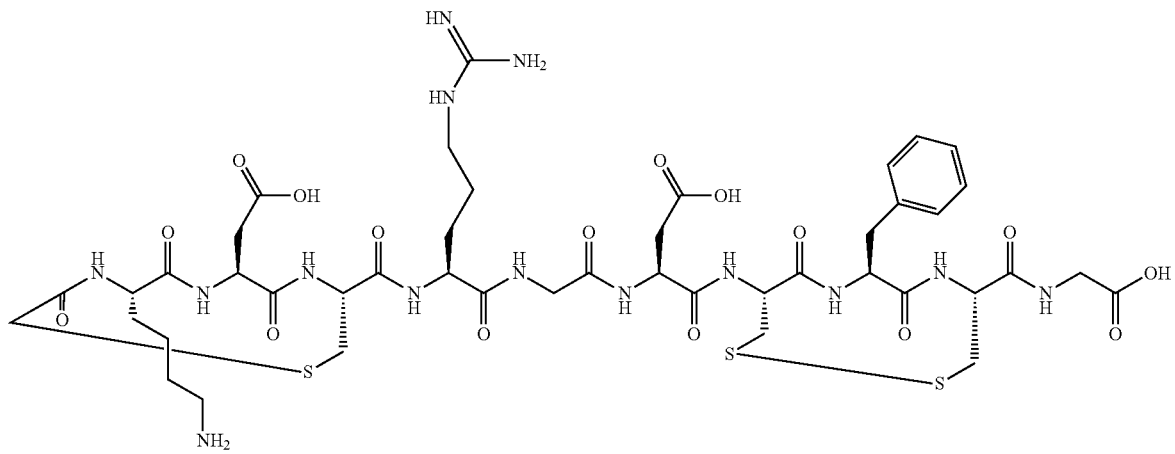

Compound 3: Example of a V-L-R compound of formula I
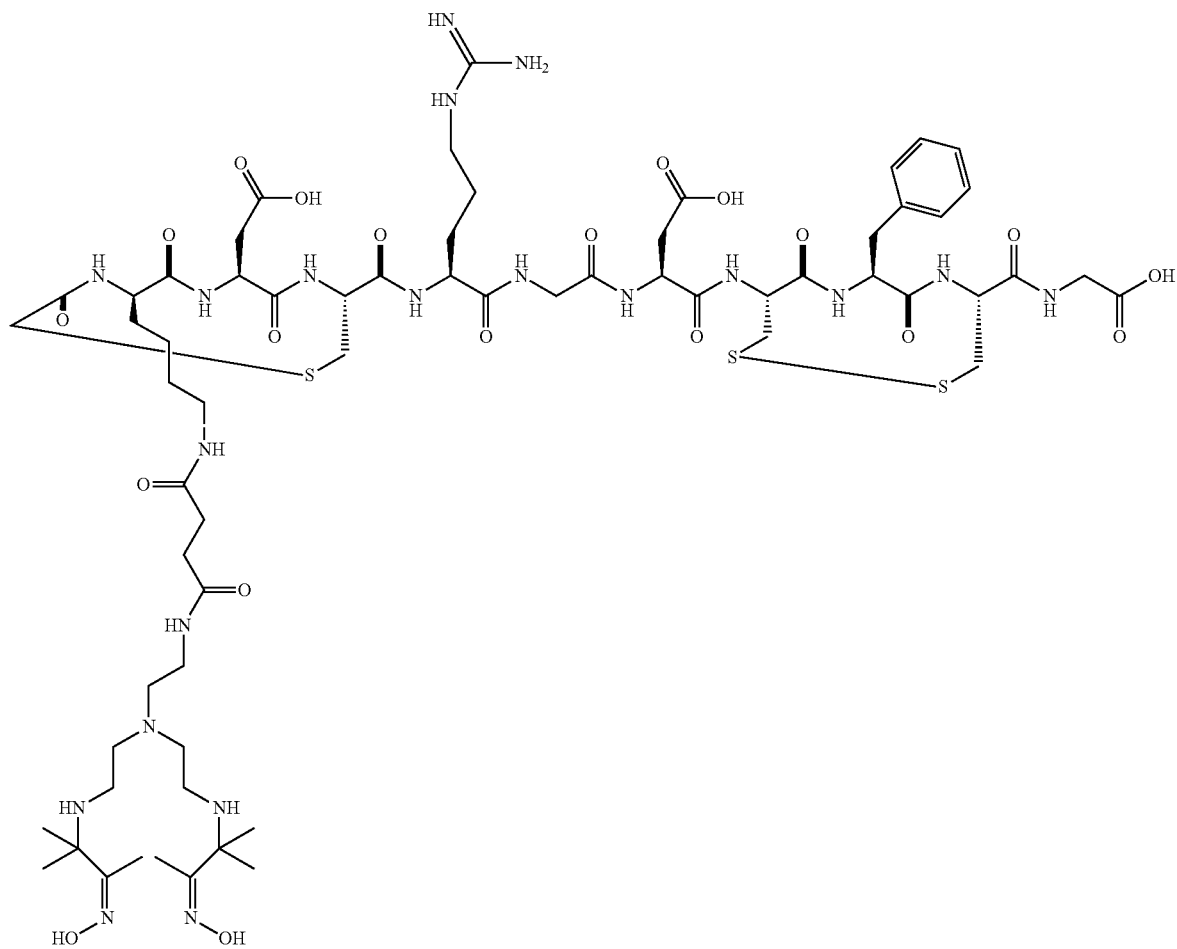
Compound 4: Example of a compound of formula II
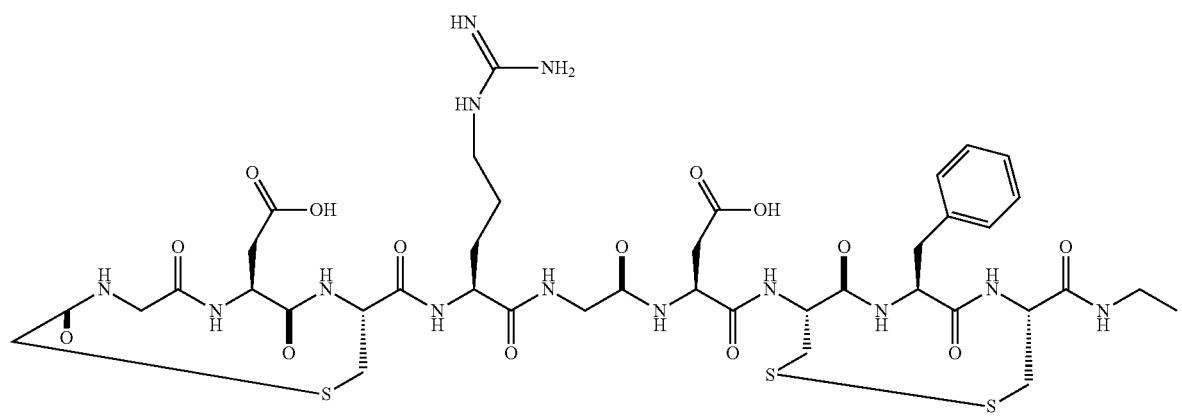

-continued

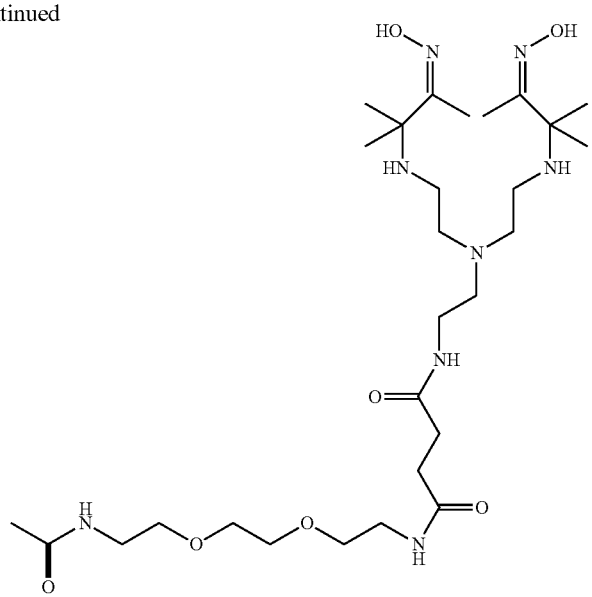

Compound 5: Example of a compound of formula capable e.g. of binding $^{99m}$Tc.

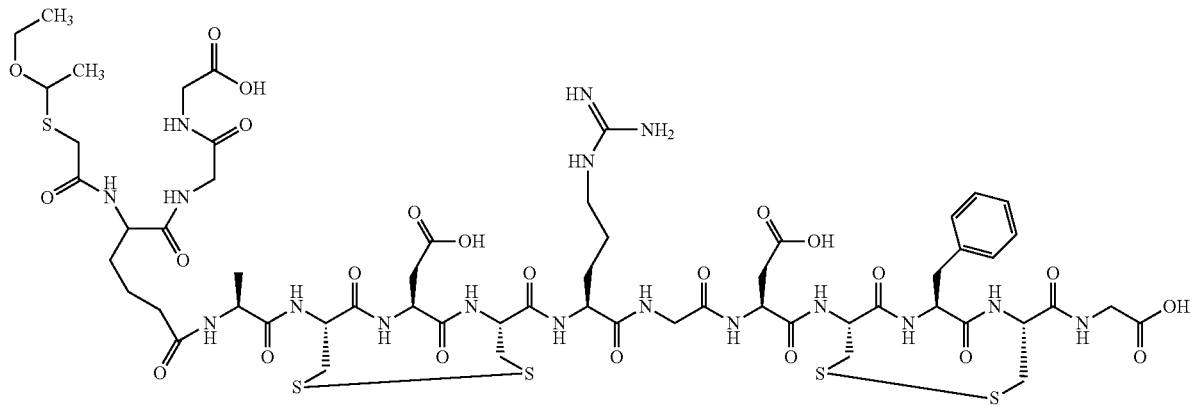

25

In most cases, it is preferred that the amino-acids in the vector V are in the L-form. However, in some embodiments of the invention one, two, three or more of the amino-acids in the vector V are preferably in the D-form. The inclusion of such D-form amino-acids can have a significant effect on the serum stability of the vector. Reference is particularly made in this regard to vectors having D-tyrosine at position $X_1$.

The invention also provides a pharmaceutical composition comprising an effective amount (e.g. an amount effective to enhance image contrast in in vivo imaging and/or for therapeutic treatment) of a compound of general formula (I) or an acid addition salt thereof, together with one or more pharmaceutically acceptable adjuvants, excipients or diluents.

As mentioned above, the compounds of formula I may comprise vector, linker and reporter moieties. A linker moiety may serve to link one vector to one reporter; alternatively it may link together more than one vector and/or more than one reporter. Likewise a reporter or a vector may be linked to more than one linker. Use in this way of a plurality of reporters (e.g. several linker-reporter moieties attached to one vector or several reporters attached to one linker itself attached to one vector) may enable the detectability of the contrast agent to be increased (e.g. by increasing its radioopacity, echogenicity or relaxivity) or may enable it to be detected in more than one imaging modality. Use in this way of a plurality of vectors may increase the targeting efficiency of the contrast agent or may make the contrast agent able to target more than one site, e.g. different receptors for an agent which has receptor heterogeneity.

Linker

A wide variety of linkers can be used, including biodegradable linkers and biopolymers.

The linker component of the contrast agent is at its simplest a bond between the vector and reporter moieties. More generally however the linker will provide a mono- or multimolecular skeleton covalently or non-covalently linking one or more vectors to one or more reporters, e.g. a linear, cyclic, branched or reticulate molecular skeleton, or a molecular aggregate, with in-built or pendant groups which bind covalently or non-covalently, e.g. coordinatively, with the vector and reporter moieties or which encapsulate, entrap or anchor such moieties. Thus linking of a reporter unit to a desired vector may be achieved by covalent or non-covalent means, usually involving interaction with one or more functional groups located on the reporter and/or vector. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups.

It will be appreciated that functional groups in the reporter and/or vector may if desired be converted to other functional groups prior to reaction, e.g. to confer additional reactivity or selectivity.

Vector-reporter coupling may also be effected using enzymes as zero-length crosslinking agents; thus, for example, transglutaminase, peroxidase and xanthine oxidase have been used to produce crosslinked products. Reverse proteolysis may also be used for crosslinking through amide bond formation.

Non-covalent vector-reporter coupling may, for example, be effected by electrostatic charge interactions, through chelation in the form of stable metal complexes or through high affinity binding interaction.

A vector which is coupled to a peptide, lipo-oligosaccharide or lipopeptide linker which contains a element capable of mediating membrane insertion may also be useful.

Coupling may also be effected using avidin or streptavidin, which have four high affinity binding sites for biotin. Avidin may therefore be used to conjugate vector to reporter if both vector and reporter are biotinylated.

So-called zero-length linking agents, which induce direct covalent joining of two reactive chemical groups without introducing additional linking material may, if desired, be used in accordance with the invention.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate.

The nature of extrinsic material introduced by the linking agent may have a critical bearing on the targeting ability, pharmacokinetics and general stability of the ultimate product. Thus it may be desirable to introduce labile linkages, e.g. containing spacer arms which are biodegradable or chemically sensitive or which incorporate enzymatic cleavage sites. Alternatively the spacer may include polymeric components, e.g. to act as surfactants and enhance the stability of the agent. The spacer may also contain reactive moieties, e.g. as described above to enhance surface crosslinking.

Spacer elements may also comprise macromolecular structures such as dextran and poly(ethyleneglycols), usually referred to as PEGs. In addition to spacer elements, PEGs may also be used to modify the in vivo characteristics of the vectors.

The major mechanism for uptake of particles by the cells of the reticuloendothelial system (RES) is opsonisation by plasma proteins in blood; these mark foreign particles which are then taken up by the RES. The biological properties of PEG spacer elements used in accordance with the invention may serve to increase the circulation time of the agent in a similar manner to that observed for PEGylated liposomes. Increased coupling efficiency to areas of interest may also be achieved using antibodies bound to the terminii of PEG spacers.

Other representative spacer elements include structural-type polysaccharides, storage-type polysaccharides, polyamino acids and methyl and ethyl esters thereof, and polypeptides, oligosaccharides and oligonucleotides, which may or may not contain enzyme cleavage sites.

Preferred linking groups are derived from vector reactive groups selected from but not limited to:

a group that will react directly with carboxy, aldehyde, amine (NHR), alcohols, sulfhydryl groups, activated methylenes and the like, on the vector, for example, active halogen containing groups, a group that can react readily with modified vector molecules containing a vector reactive group, i.e., vectors containing a reactive group modified to contain reactive groups, for example, by oxidation of the vector to an aldehyde or a carboxylic acid, and a group that can be linked to the vector containing a reactive group, or to the modified vector as noted above by use of a crosslinking agent.

Preferred useful linking groups are derived from various heterobifunctional cross-linking reagents such as those listed in the Pierce Chemical Company Immunotechnology Catalog—Protein Modification Section, (1995 and 1996).

In addition to the foregoing description, the linking groups, in whole or in part, can also be comprised of and derived from complementary sequences of nucleotides and residues of nucleotides, both naturally occurring and modified, preferably non-self-associating oligonucleotide sequences.

Linking agents used in accordance with the invention will in general bring about linking of vector to reporter or reporter to reporter with some degree of specificity, and may also be used to attach one or more therapeutically active agents.

Further examples of the linkers which may be used in the context of the current application are given on pages 32-54 of WO98/47541 and the disclosures made on these pages are incorporated herein by reference in their entirety. It is hereby asserted that each and every linker or part thereof disclosed on the aforementioned pages is considered to be part of the description of the invention contained in this application.

Reporter

The reporter moieties in the contrast agents of the invention may be any moiety capable of detection either directly or indirectly in an in vivo diagnostic imaging procedure, e.g. moieties which emit or may be caused to emit detectable radiation (e.g. by radioactive decay, fluorescence excitation, spin resonance excitation, etc.), moieties which affect local electromagnetic fields (e.g. paramagnetic, superparamagnetic, ferrimagnetic or ferromagnetic species), moieties which absorb or scatter radiation energy (e.g. chromophores and fluorophores), particles (including liquid containing vesicles), heavy elements and compounds thereof, and moieties which generate a detectable substance, etc..

A very wide range of materials detectable by diagnostic imaging modalities is known from the art and the reporter will be selected according to the imaging modality to be used. Thus for example for ultrasound imaging an echogenic material, or a material capable of generating an echogenic material will normally be selected. The vectors may be coupled via a linker to a suitable lipid reporter/carrier for incorporation into a gas-filled microbubble. Such microbubbles may be used for targeting ultrasound imaging.

For X-ray imaging the reporter will generally be or contain a heavy atom (e.g. of atomic weight 38 or above). For MR imaging the reporter will either be a non zero nuclear spin isotope (such as $^{19}F$) or a material having unpaired electron spins and hence paramagnetic, superparamagnetic, ferrimagnetic or ferromagnetic properties. For light imaging the reporter will be a light scatterer (e.g. a coloured or uncoloured particle), a light absorber or a light emitter. For magnetometric imaging the reporter will have detectable magnetic properties; for electrical impedance imaging the reporter will affect electrical impedance. For scintigraphy, SPECT, PET, etc., the reporter will be a radionuclide.

Examples of suitable reporters are widely known from the diagnostic imaging literature, e.g. magnetic iron oxide particles, X-ray contrast agent containing vesicles, chelated paramagnetic metals (such as Gd, Dy, Mn, Fe etc.). See for example U.S. Pat. No. 4,647,447, PCT/GB97/00067, U.S. Pat. Nos. 4,863,715, 4,770,183, WO96/09840, WO85/02772, WO92/17212, PCT/GB97/00459, EP-A-554213, U.S. Pat. No. 5,228,446, WO91/15243, WO93/05818, WO96/23524, WO96/17628, U.S. Pat. No. 5,387,080, WO95/26205, GB9624918.0, etc. See also WO 98/47541 (pages 63-66 and 70-86).

Particularly preferred as reporters are: chelated paramagnetic metal ions such as Gd, Dy, Fe, and Mn, especially when chelated by macrocyclic chelant groups.

Stated generally, the reporter may be (1) a chelatable metal or polyatomic metal-containing ion (i.e. TcO, etc), where the metal is a high atomic number metal (e.g. atomic number greater than 37), a paramagentic species (e.g. a transition metal or lanthanide), or a radioactive isotope, (2) a covalently bound non-metal species which is an unpaired electron site (e.g. an oxygen or carbon in a persistant free radical), a high atomic number non-metal, or a radioisotope, (3) a polyatomic cluster or crystal containing high atomic number atoms, displaying cooperative magnetic behaviour (e.g. superparamagnetism, ferrimagnetism or ferromagnetism) or containing radionuclides, (4) a chromophore (by which term species which are fluorescent or phosphorescent are included), e.g. an inorganic or organic structure, particularly a complexed metal ion or an organic group having an extensive delocalized electron system, or (5) a structure or group having electrical impedance varying characteristics, e.g. by virtue of an extensive delocalized electron system.

Examples of particular preferred reporter groups are described in more detail below.

Chelated metal reporters: metal radionuclides, paramagnetic metal ions, fluorescent metal ions, heavy metal ions and cluster ions.

Preferred metal radionuclides include $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$.

Preferred paramagnetic metal ions include ions of transition and lanthanide metals (e.g. metals having atomic numbers of 6 to 9, 21-29, 42, 43, 44, or 57-71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

The metal ions are desirably chelated by chelant groups on the linker moiety or in or on a particle, (e.g. a vesicle or a porous or non-porous inorganic or organic solid), in particular linear, macrocyclic, terpyridine and $N_2S_2$ chelants, such as for example DTPA, DTPA-BMA, EDTA, D03A and TMT. Further examples of suitable chelant groups are disclosed in U.S. Pat. No. 4,647,447, WO89/00557, U.S. Pat. No. 5,367,080, U.S. Pat. No. 5,364,613, etc..

The linker moiety or the particle may contain one or more such chelant groups, if desired metallated by more than one metal species (e.g. so as to provide reporters detectable in different imaging modalities).

Other suitable residues of chelating agents comprise proteins modified for the chelation of metals such as technetium and rhenium as described in U.S. Pat. No. 5,078,985, the disclosure of which is hereby incorporated by reference.

Methods for metallating any chelating agents present are within the level of skill in the art. Metals can be incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so as not to interfere with the binding of the metal ion with the chelating agent. The chelating agent-containing moiety is preferably in aqueous solution at a pH of between about 5 and about 9, more preferably between pH about 6 to about 8. The chelating agent-containing moiety can be mixed with buffer salts such as citrate, acetate, phosphate and borate to produce the optimum pH.

Preferably, the buffer salts are selected so as not to interfere with the subsequent binding of the metal ion to the chelating agent.

In diagnostic imaging, the vector-linker-reporter (VLR) construct preferably contains a ratio of metal radionuclide ion to chelating agent that is effective in such diagnostic imaging applications. In preferred embodiments, the mole ratio of metal ion per chelating agent is from about 1:1,000 to about 1:1.

In radiotherapeutic applications, the VLR preferably contains a ratio of metal radionuclide ion to chelating agent that is effective in such therapeutic applications. In preferred embodiments, the mole ratio of metal ion per chelating agent is from about 1:100 to about 1:1. The radionuclide can be selected, for example, from radioisotopes of Sc, Fe, Pb, Ga, Y, Bi, Mn, Cu, Cr, Zn, Ge, Mo, Ru, Sn, Sr, Sm, Lu, Sb, W, Re, Po, Ta and Tl. Preferred radionuclides include $^{44}Sc$, $^{64}Cu$, $^{67}Cu$, $^{212}Pb$, $^{68}Ga$, $^{90}Y$, $^{153}Sm$, $^{212}Bi$, $^{186}Re$ and $^{188}Re$. Of these, especially preferred is $^{90}Y$. These radioisotopes can be atomic or preferably ionic.

The following isotopes or isotope pairs can be used for both imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

The linker moiety may also allow for coupling to a plurality of chelant groups. The chelant moieties within such a polychelant linker may be attached via backbone functionalization of the chelant or by utilization of one or more of the metal co-ordinating groups of the chelant or by amide or ether bond formation between acid chelant and an amine or hydroxyl carrying linker backbone, e.g. as in polylysine-polyDTPA, polylysine-polyDOTA and in the so-called magnifier polychelants, of PCT/EP96/00565. Such polychelant linkers may be conjugated to one or more vector groups either directly (e.g. utilizing amine, acid or hydroxyl groups in the polychelant linker) or via a bifunctional linker compound as discussed above for monochelant linkers.

Where the chelated species is carried by a particulate (or molecular aggregate, e.g. vesicular) linker, the chelate may for example be an unattached mono or polychelate (such as Gd DTPA-BMA or Gd HP-DO3A) enclosed within the particle or it may be a mono or polychelate conjugated to the particle either by covalent bonding or by interaction of an anchor group (e.g. a lipophilic group) on the mono/polychelate with the membrane of a vesicle (see for example PCT/GB95/02378).

Preferred non-metal atomic reporters include radioisotopes such as $^{123}I$ and $^{131}I$ as well as non zero nuclear spin atoms such as $^{19}F$, and heavy atoms such as I.

Such reporters, preferably a plurality thereof, e.g. 2 to 200, may be covalently bonded to a linker backbone, either directly using conventional chemical synthesis techniques or via a supporting group, e.g. a triiodophenyl group.

In an embodiment of this invention, the use of radioisotopes of iodine is specifically contemplated. For example, if the vector or linker is comprised of substituents that can be chemically substituted by iodine in a covalent bond forming reaction, such as, for example, substituents containing hydroxyphenyl functionality, such substituents can be labeled by methods well known in the art with a radioisotope of iodine. The iodine species can be used in therapeutic and diagnostic imaging applications. While, at the same time, a metal in a chelating agent on the same vector-linker can also be used in either therapeutic or diagnostic imaging applications. As with the metal chelants discussed above, such metal atomic reporters may be linked to the linker or carried in or on a particulate linker, e.g. in a vesicle (see WO95/26205 and GB 9624918.0).

Linkers of the type described above in connection with the metal reporters may be used for non-metal atomic reporters with the non-metal atomic reporter or groups carrying such reporters taking the place of some or all of the chelant groups.

Preferably the V-L-R agents of the invention will have the receptor targetting vectors coupled directly or indirectly to a reporter, e.g. with covalently bound iodine radioisotopes, with metal chelates attached directly or via an organic linker group or coupled to a particulate reporter or linker-reporter, e.g. a superparamagnetic crystals (optionally coated, e.g. as in PCT/GB97/00067), or a vesicle, e.g. an iodinated contrast agent containing micelle or liposome.

Put briefly, for the imaging modalities of MRI, X-ray, light imaging, nuclear imaging, magnetotomography and electrical impedance tomography, the favoured reporters may be as follows:

| | |
|---|---|
| MRI | Superparamgnetic iron oxide particles, in general having a particle size smaller than about 80 nm and especially those with a size less than 20 nm. In particular iron oxides coated with various coating materials such as polyelectrolytes, PEG, starch and hyrolyzed starch are preferred. Paramagnetic metal substances including both chelates and particulate materials are also useful. |
| Light imaging | Any light imaging reporter group. The focus should be on substances absorbing in the near infrared range. |
| Nuclear medicine | Radioactive chelates comprising $^{99}$Tc or $^{111}$In as well as direct radiolabelled vectors having radiolabelled halogens substituents such as $^{123}$I, $^{125}$I, $^{131}$I, $^{75}$Br or $^{77}$Br. |
| Magnetotomography | Superparamagnetic iron oxide particles as described above. |
| Electrical impedance tomography | Polyionic species, e.g. polymers with ionic groups in the repeat units. |

A preferred embodiment of the invention relates to a radiolabelled agent of general formula (I), particularly for use in tumour imaging.

The diagnostic agents of the invention may be administered to patients for imaging in amounts sufficient to yield the desired contrast with the particular imaging technique. Where the reporter is a metal, generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight. Where the reporter is a radionuclide, dosages of 0.01 to 100 mCi, preferably 0.1 to 50 mCi will normally be sufficient per 70 kg bodyweight. Where the reporter is a superparamagnetic particle, the dosage will normally be 0.5 to 30 mg Fe/kg bodyweight.

The dosage of the compounds of the invention for therapeutic use will depend upon the condition being treated, but in general will be of the order of from 1 pmol/kg to 1 mmol/kg bodyweight.

The compounds according to the invention may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

The agents of formula I may be therapeutically effective in the treatment of disease states as well as detectable in in vivo imaging. Thus for example the vector of the VLR compound may have therapeutic efficacy, e.g. by virtue of the radiotherapeutic effect of a radionuclide reporter, the efficacy in photodynamic therapy of a chromophore (or fluorophore) reporter or the chemotherapeutic effect of the vector moiety.

Use of the agents of formula I in the manufacture of therapeutic compositions and in methods of therapeutic or prophylactic treatment of the human or non-human animal body are thus considered to represent further aspects of the invention.

Viewed from a further aspect the invention provides the use of an agent of formula I for the manufacture of a contrast medium for use in a method of diagnosis involving administration of said contrast medium to an animate subject and generation of an image of at least part of said subject.

Viewed from a still further aspect the invention provides a method of generating an image of an animate human or non-human (preferably mammalian or avian) animal subject involving administering a contrast agent to said subject, e.g. into the vascular system and generating an image of at least a part of said subject to which said contrast agent has distributed, e.g. by X-ray, MR, ultrasound, scintigraphy, PET, SPECT, electrical impedance, light or magnetometric imaging modalities, characterised in that as said contrast agent is used an agent of formula I.

Viewed from a further aspect the invention provides a method of monitoring the effect of treatment of a human or non-human animal subject with a drug to combat a condition associated with angiogenesis, e.g. a cytotoxic agent, said method involving administering to said subject an agent of formula I and detecting the uptake of said agent by endothelial cell receptors, in particular $\alpha v \beta 3$ receptors, said administration and detection optionally but preferably being effected repeatedly, e.g. before, during and after treatment with said drug.

Viewed from a yet further aspect the invention provides a process for the preparation of an agent of formula I, said process comprising the conjugation of a vector V to a compound detectable in a diagnostic imaging procedure or a chelant compound and if necessary metallating chelant groups in the resultant conjugate with a metal ion detectable in a diagnostic imaging procedure.

Viewed from yet another aspect the invention provides a process for the preparation of an agent of formula I, for therapeutic treatment, said process comprising the conjugation of a vector V to a compound to be therapeutically effective in the treatment of disease states.

The vectors of the present invention can be synthesised using all the known methods of chemical synthesis but particularly useful is the solid-phase methodology of Merrifield employing an automated peptide synthesiser (J. Am. Chem. Soc., 85: 2149 (1964)). Vectors containing multiple disulphide bridges are synthesised using differential cysteine protecting groups so that no ambiguity exists as to the final folded form of the vector. The peptides and peptide chelates may be purified using high performance liquid chromatography (HPLC) and characterised by mass spectrometry and analytical HPLC before testing in the in vitro screen.

There follows a series of non-limitive examples:

EXAMPLE 1

Synthesis of Compound 1:

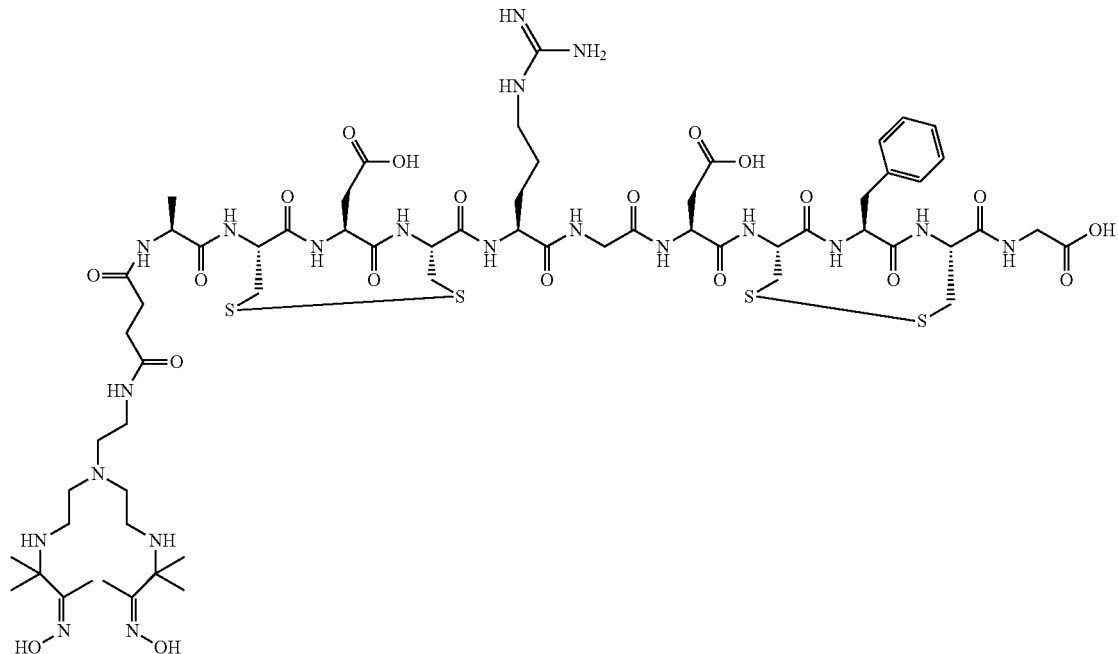

Synthesis of technetium chelate—Pn216
a) Chloro-nitroso Intermediate (3-chloro-3-methyl-2-nitrosobutane)

A mixture of 2-methylbut-2-ene (18.5 mL) and iso-amyl nitrate (19.5 mL) was stirred, cooled to −10° C. and concentrated hydrochloric acid (17.5 mL) added carefully to maintain the temperature below 0° C. The reaction was stirred at this temperature for 30 minutes. The precipitate formed was collected by filtration, washed 4×5 mL of ethanol (−20° C.) and dried in vacuo to give 3-chloro-3-methyl-2-nitrosobutane as a white solid.

b) Pn216-(3,3,11,11-tetramethyl-7-aminoethyl-4,7,10,triazatridecane-2,12-dionedioxime)

To a solution of tris-(2-aminoethyl) amine in acetonitrile (20 mL) was added sodium bicarbonate (2.2 g, 26 mmol). A solution of 3-chloro-3-methyl-2-nitrosobutane (1.8 g, 13 mmol) in dry acetonitrile was added slowly at 0° C. The reaction mixture was left to stir at room temperature for 4 hours and then filtered. The filtrant was washed with acetonitrile and the filtrate evaporated. The crude product was dissolved in acetonitrile and purified by HPLC to afford Pn216. Yield 0.88 g, 19% c) Synthesis of Pn216-Succinic Acid Intermediate:

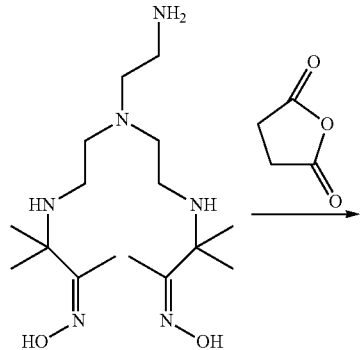

-continued

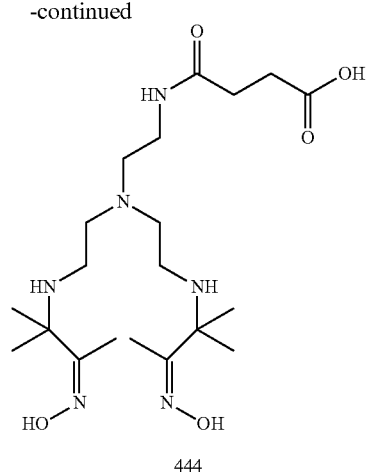

444

Succinic anhydride (100)
Pn216 (358)
Tetrafluorothiophenol (182)
DCCI (206)

Pn216 (0.5 g, 1.4 mmol) was dissolved in DMF (5 mL) and succinic anhydride (0.015 g, 1.5 mmol) in DMF (10 mL) added portionwise with stirring. The reaction was left stirring for 16 hours to afford complete conversion to the desired product. The pure acid was obtained following HPLC chromatography in good yield.

d) Synthesis of the Tetrafluorothiophenol Ester Derivative of Pn216-Succinic Acid

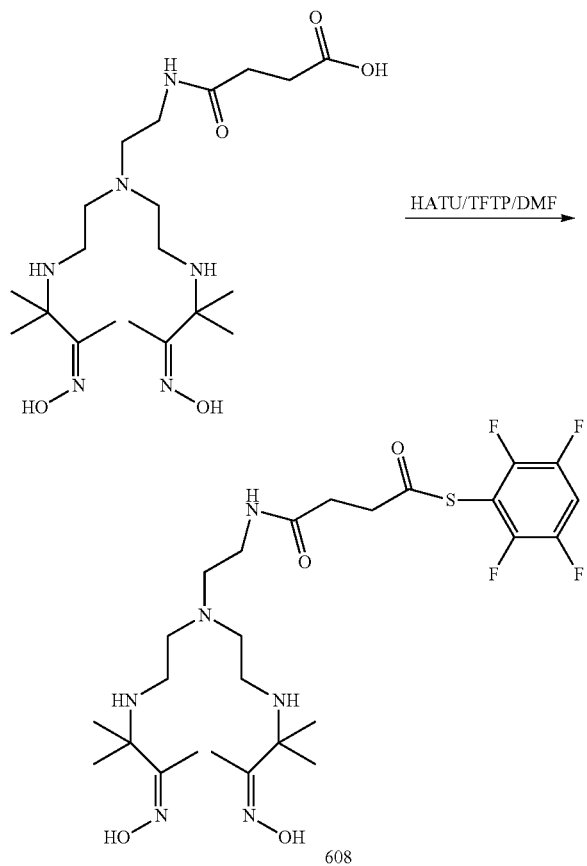

HATU [O-(7-azabenzotriazol-1-yl)-1,1,3,3-tetramethyluronium hexafluorophosphate]—Mwt=380
Pn216—NH—CO—(CH2)$_2$—COOH—Mwt=458
NMM—N-methylmorpholine—Mwt=101
TFTP—tetrafluorothiophenol—Mwt=182

To Pn216 acid (10 mg, 0.022 mmol) in DMF (1.0 mL) was added HATU (8.3 mg, 0.022 mmol) and NMM (0.007 mL, 0.066 mmol). The mixture was stirred for 5 minutes then TFTP (0.022 mmol, 4 mg) added. The solution was stirred for 30 minutes then the reaction mixture was diluted with 20% acetonitrile/H$_2$O (3 mL) and the product purified by reverse-phase chromatography yielding 6 mg of the desired product following freeze-drying.

e) Synthesis of Peptide Vector NH$_2$-Ala-Cys-Asp-Cys-Arg-Gly-Asp-Cys-Phe-Cys-Gly-OH (Seq. ID 1) with disulphide bonds connecting Cys 2 and 4; Cys 8 and 10

The peptide was synthesised on a ABI 433A automatic peptide synthesiser starting with Fmoc-Gly Wang resin (Novabiochem) on a 0.1 mmol scale using 1 mmol amino acid cartridges. Cysteine residues 2 and 4 were S-protected using trityl protection while 8 and 10 were protected with acetamidomethyl (Acm) protection. The amino acids were pre-activated using HBTU before coupling. The simultaneous removal of peptide and side-chain protecting groups (except Acm) from the resin was carried out in TFA containing TIS (5%), H$_2$O (5%) and phenol (2.5%) for two hours.

After work-up 100 mg of partially protected crude peptide was obtained (Analytical HPLC: Gradient, 0-30% B over 20 min where A=H$_2$O/0.1% TFA and B=CH$_3$CN/0.1% TFA; column, VYDAC C18 218TP54; detection, UV 214 nm; product retention time, 16.7 min). An aliquot of crude product (25 mg) was then purified by Prep. HPLC Vydac column yielding 12.5 mg of pure partially protected peptide.

The first disulphide bond between Cys2 and Cys4 was formed by dissolving the pure intermediate in 20 mL of 2.5% DMSO/TFA solution. After 40 minutes a new peak had appeared corresponding to the oxidised product. To the peptide solution was then added anisole (0,02 mL) and the solution warmed to 60° C. for 50 minutes. Excess TFA was then removed in vacuo and the product precipitated following addition of diethyl ether. A further Prep. HPLC step was carried out and pure product collected and freeze-dried. MALDI-TOF analysis was used to confirm molecular weight and a co-injection with the two other possible disulphide isomers performed to confirm identity.

f) Synthesis of Compound 1:

Peptide from section e) above is dissolved together with Pn216 active ester from section d) above in DMF in a 1:2 ratio (w:w). The reaction is left stirring for 2 days then the mixture is diluted with water and the desired product purified out by reverse-phase HPLC.

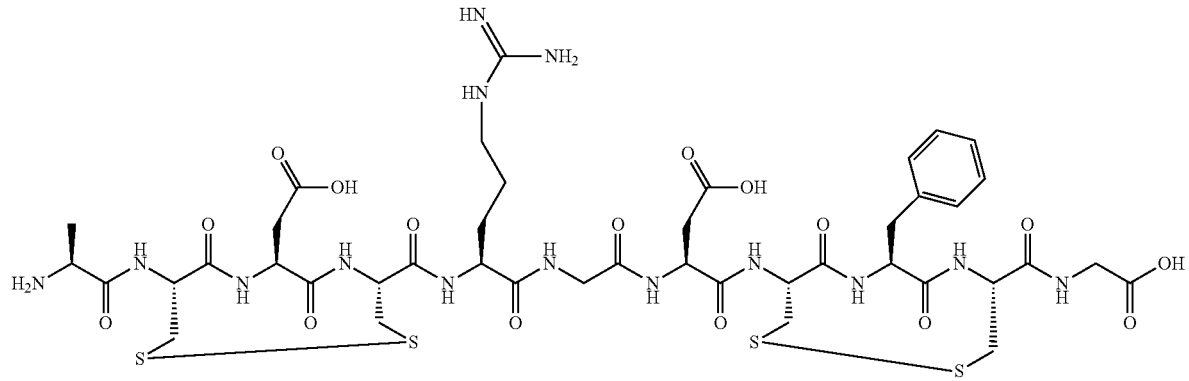

EXAMPLE 2

[Cys[2-4, 8-10]] Analogues a) Synthesis of ClCH$_2$CO-Lys-Asp-Cys-Arg-Gly-Asp-Cys(tBu)-Phe-Cys(tBu)-Gly-Gly-OH (Seq. ID 2)

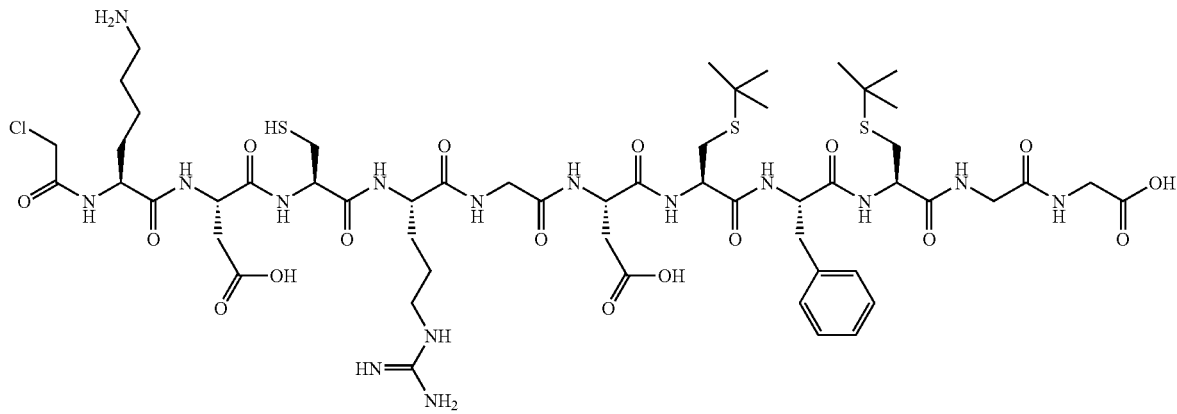

The peptide was synthesised on an ABI 433A automatic peptide synthesiser starting with Fmoc-Gly-Wang resin on a 0.25 mmol scale using 1 mmol amino acid cartridges. The amino acids were pre-activated using HBTU before coupling. Final N-terminal chloroacetylation was accomplished using a solution of chloroacetic anhydride in DMF for 30 min.

The simultaneous removal of peptide and side-chain protecting groups (except tBu) from the resin was carried out in TFA containing TIS (5%), H$_2$O (5%) and phenol (2.5%) for two hours.

After work-up 260 mg of crude peptide was obtained (Analytical HPLC: Gradient, 5-50% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 6.5 min. Further product characterisation was carried out using mass spectrometry: Expected, M+H at 1348.5, found, at 1348.5).

b) Synthesis of cyclo [CH$_2$CO-Lys-Asp-Cys]-Arg-Gly-Asp-Cys(tBu)-Phe-Cys(tBu)-Gly-Gly-OH (Seq. ID 2)

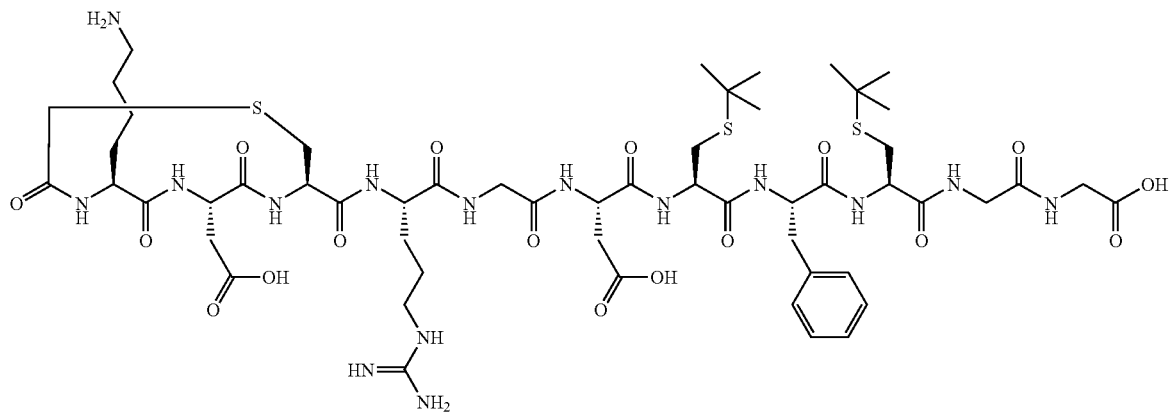

100 mg ClCH$_2$CO-Lys-Asp-Cys-Arg-Gly-Asp-Cys(tBu)-Phe-Cys(tBu)-Gly-Gly-OH) was dissolved in water/acetonitrile. The mixture was adjusted to pH 8 with ammonia solution and stirred for 24 hours.

After work-up crude peptide was obtained (Analytical HPLC: Gradient, 5-50% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 6.32 min. Further product characterisation was carried out using mass spectrometry: Expected, M+H at 1312.5, found, at 1312.6).

c) Synthesis of [Cys$^{7-9}$] cyclo [CH$_2$CO-Lys-Asp-Cys]-Arg-Gly-Asp-Cys -Phe-Cys-Gly-Gly-OH

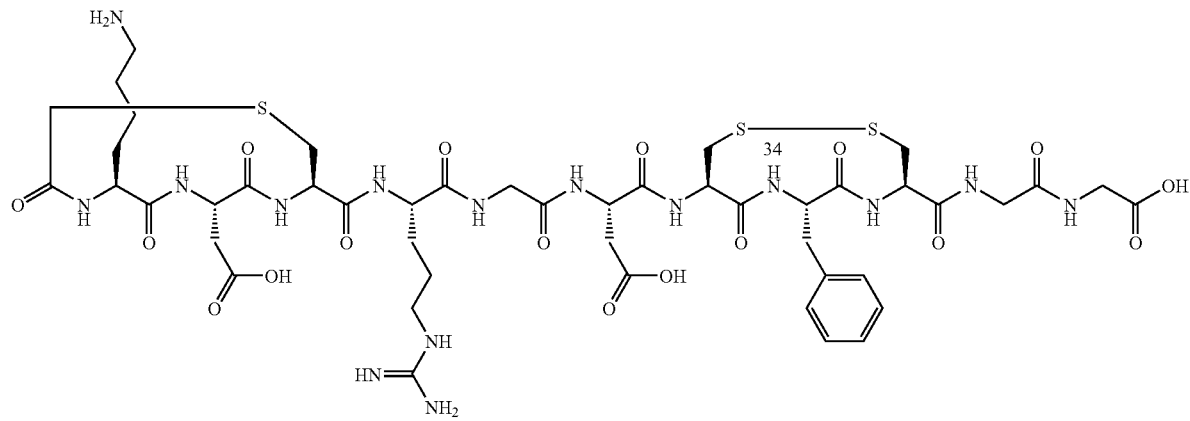

40 mg of cyclo[CH$_2$CO-Lys-Asp-Cys]-Arg-Gly-Asp -Cys (tBu)-Phe-Cys(tBu)-Gly-Gly-OH (Seq. ID 2) was treated with a solution of anisole (200 µL), DMSO (1 mL) and TFA (50 mL) for 30 min following which the TFA was removed in vacuo and the peptide precipitated by the addition of diethyl ether.

Purification by preparative HPLC (Phenomenex Luna 5µ C18 (2) 250×21.20 mm column) of the crude material (40 mg) was carried out using 0-30% B, where A=H$_2$O/0.1% TFA and B=CH$_3$CN/0.1% TFA, over 40 min at a flow rate of 10 mL/min. After lyophilisation 14.3 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 6.10 min. Further product characterisation was carried out using mass spectrometry: Expected, M+H at 1198.4, found, at 1198.5).

d) Conjugation of [Cys$^{7-9}$] cyclo[CH$_2$CO-Lys-Asp-Cys]-Arg-Gly -Asp-Cys-Phe-Cys-Gly-Gly-OH (Seq ID 2)and Pn216-succinic acid

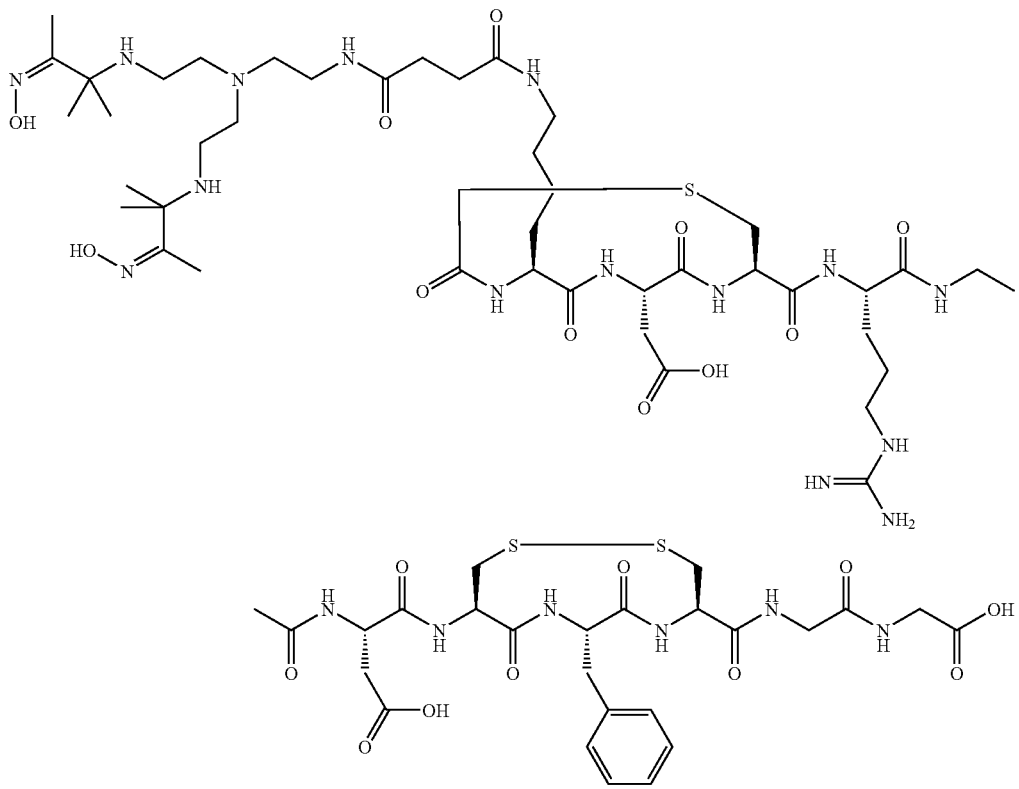

[Cys$^{7-9}$] cyclo[CH$_2$CO-Lys-Asp-Cys]-Arg-Gly-Asp-Cys-Phe -Cys-Gly-Gly-OH (Seq ID 2), Pn216 chelate active ester and N-methylmorpholine is dissolved in DMF. The mixture is stirred until complete conjugation is observed by RP-HPLC monitoring.

Purification by preparative RP-HPLC of the reaction mixture is carried out to afford pure material following lyophilisation. Product characterisation is carried out using RP-HPLC and mass spectrometry.

What is claimed is:

1. A compound according to general formula (II)

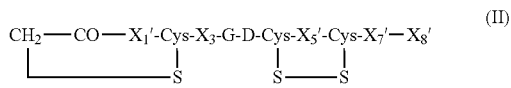

wherein:

Cys=Cysteine $X_1'$ is 1, 2 or 3 amino-acids, independently selected from the group consisting of aspartic acid, tyrosine, tyrosine-aspartic acid, lysine or acetyl-lysine, or mixtures thereof;

$X_3$ is arginine or N-methylarginine;

$X_5'$ is phenylalanine, tyrosine, 3-iodo-tyrosine or naphthylalanine;

$X_7'$ is a bond, glycine, or a O-bis(aminoethyl)ethylene glycol spacer; and $X_8'$ is a chelate binding to a metal radionuclide wherein the structure of the chelate is.

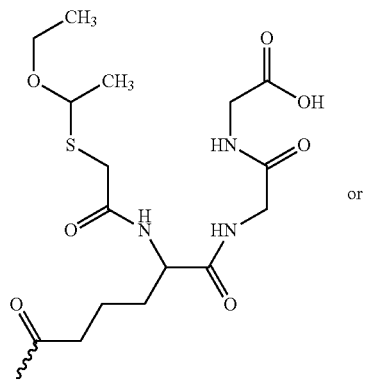

or

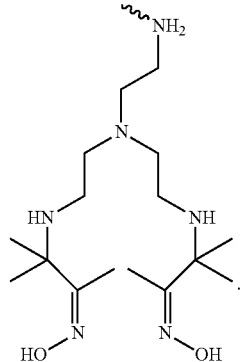

2. A compound as claimed in claim 1 wherein $X_1'$ is aspartic acid, tyrosine, tyrosine-aspartic acid, lysine or acetyl-lysine 3. A compound as claimed in claim 1 wherein $X_7'$ is glycine.

4. A method of making a therapeutic compositions or a contrast medium, said method comprising adding the compound of claim 1 with physiologically acceptable carriers or excipients.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial sequence
<220> FEATURE:
<223> OTHER INFORMATION: synthetic peptide

<400> SEQUENCE: 1

Ala Cys Asp Cys Arg Gly Asp Cys Phe Cys Gly
1               5                   10

<210> SEQ ID NO 2
<211> LENGTH: 11
<212> TYPE: PRT
<213> ORGANISM: Artificial sequence
<220> FEATURE:
<223> OTHER INFORMATION: synthetic peptide

<400> SEQUENCE: 2

Lys Asp Cys Arg Gly Asp Cys Phe Cys Gly Gly
1               5                   10
```